(12) United States Patent
Meulink

(10) Patent No.: US 6,330,845 B1
(45) Date of Patent: Dec. 18, 2001

(54) WRENCH FOR AN IMPLANT

(75) Inventor: Steven L. Meulink, Warsaw, IN (US)

(73) Assignee: Bristol-Myers Squibb, New York, NY (US)

( * ) Notice: Subject to any disclaimer, the term of this patent is extended or adjusted under 35 U.S.C. 154(b) by 0 days.

(21) Appl. No.: 09/572,347

(22) Filed: May 17, 2000

(51) Int. Cl.$^7$ .................................................. B25B 23/00
(52) U.S. Cl. .......................... 81/462; 81/180.1; 606/104; 623/22.12
(58) Field of Search .................. 81/462, 180.1; 606/104; 623/22.12

(56) References Cited

U.S. PATENT DOCUMENTS

| | | | | |
|---|---|---|---|---|
| 2,459,672 | * | 1/1949 | Morsch | 81/462 |
| 2,679,270 | * | 5/1954 | Krause | 81/462 |
| 2,721,589 | * | 10/1955 | Hammer | 81/462 |
| 3,349,652 | * | 10/1967 | Cromwell | 81/462 |
| 5,138,914 | * | 8/1992 | Brickner | 81/180.1 X |
| 5,352,231 | * | 10/1994 | Brumfield et al. | 606/104 X |
| 5,370,022 | * | 12/1994 | Rodriguez et al. | 81/462 |
| 5,741,266 | * | 4/1998 | Moran et al. | 606/104 X |

* cited by examiner

Primary Examiner—James G. Smith
(74) Attorney, Agent, or Firm—Cary Reeves

(57) ABSTRACT

A wrench assembly used to restrain an implant while applying a torque to a portion of the implant. The wrench assembly conveniently restrains the implant relative to the torque whether the implant is implanted or not. In the case where the implant is first implanted, the wrench assembly guards against displacing the implant or splitting the bone. The wrench assembly includes a handle and a socket shaft depending from the handle in torque transmitting relation. A socket is coupled to the socket shaft in torque transmitting relation. The socket has an implant engaging portion for engaging the implant in torque transmitting relation. The socket further has a through hole aligned with the portion of the implant. A driving shaft passes through the through hole in the socket and engages the portion of the implant such that with the handle torsionaly fixed, the implant is torsionaly fixed by way of the handle, socket shaft, socket and implant connections. The driving shaft is movable relative to the socket to impart an opposing torque on the portion of the implant.

16 Claims, 8 Drawing Sheets

WRENCH FOR AN IMPLANT

BACKGROUND OF THE INVENTION

The present invention relates to a tool for assembling a multicomponent prosthesis. More particularly, the present invention relates to a tool for restraining an implant while applying a torque to a portion of the implant.

It is known in the art of orthopaedic joint replacement to provide an implant having multiple components that are assembled at the time of surgery. For example, it is known to provide a stemmed implant in which the stem is provided separately from a body portion. An example of such an implant for hip replacement surgery is taught in U.S. Pat. No. 3,067,740. An example of such an implant for knee replacement surgery is taught in U.S. Pat. No. 5,290,313. Applicant teaches an improved implant of this type in pending U.S. application Ser. No. 09/334,402. Applicant also teaches a tool for compressing such stem and body components into tight engagement in pending U.S. application Ser. No. 09/523,545. Often a threaded fastener is used to further secure the stem and body components together. A wrench is typically used to apply a torque to the threaded fastener. If the implant is inserted into a bone at the time the fastener is torqued, care must be taken not to shift the position of the implant in the bone. Likewise, care must be taken that the torque is not transmitted to the bone in such a was as to fracture the bone. Furthermore, if the implant is not implanted at the time the fastener is torqued, a way must be provided to restrain the implant so that the fastener will be tightened.

SUMMARY OF THE INVENTION

The present invention provides a wrench assembly usable to restrain an implant while applying a torque to a portion of the implant. The wrench assembly conveniently restrains the implant relative to the torque whether the implant is implanted or not. In the case where the implant is first implanted, the wrench assembly guards against displacing the implant or splitting the bone. The wrench assembly includes a handle and a socket shaft depending from the handle in torque transmitting relation. A socket is coupled to the socket shaft in torque transmitting relation. The socket has an implant engaging portion for engaging the implant in torque transmitting relation. The socket further has a through hole aligned with the portion of the implant. A driving shaft passes through the through hole in the socket and engages the portion of the implant such that with the handle torsionaly fixed, the implant is torsionaly fixed by way of the handle, socket shaft, socket and implant connections. The driving shaft is movable relative to the socket to impart an opposing torque on the portion of the implant.

In a further aspect of the invention, the wrench assembly includes a driving shaft stabilizer. The driving shaft stabilizer is spaced from the socket and has a through hole aligned with the through hole in the socket. The driving shaft passes through both the hole in the stabilizer and the hole in the socket. In a further aspect of the invention, the driving shaft stabilizer includes a plurality of through holes in an angular array relative to the socket shaft. The socket is selectively attachable to the socket shaft in alternate positions. There is a distinct alternate position corresponding to each of the plurality of through holes in the driving shaft stabilizer in which each of the corresponding through holes in the driving shaft stabilizer is alternately aligned with the through hole in the socket.

In yet another aspect of the invention, a method is provided for restraining an implant while applying a torque to the implant. The method includes providing a wrench assembly including a socket with a through hole, engaging the socket with the implant, inserting a driving shaft through the through hole, engaging the driving shaft with a portion of the implant, and applying opposing torque to the handle and driving shaft.

DETAILED DESCRIPTION OF THE INVENTION

Figure 2:
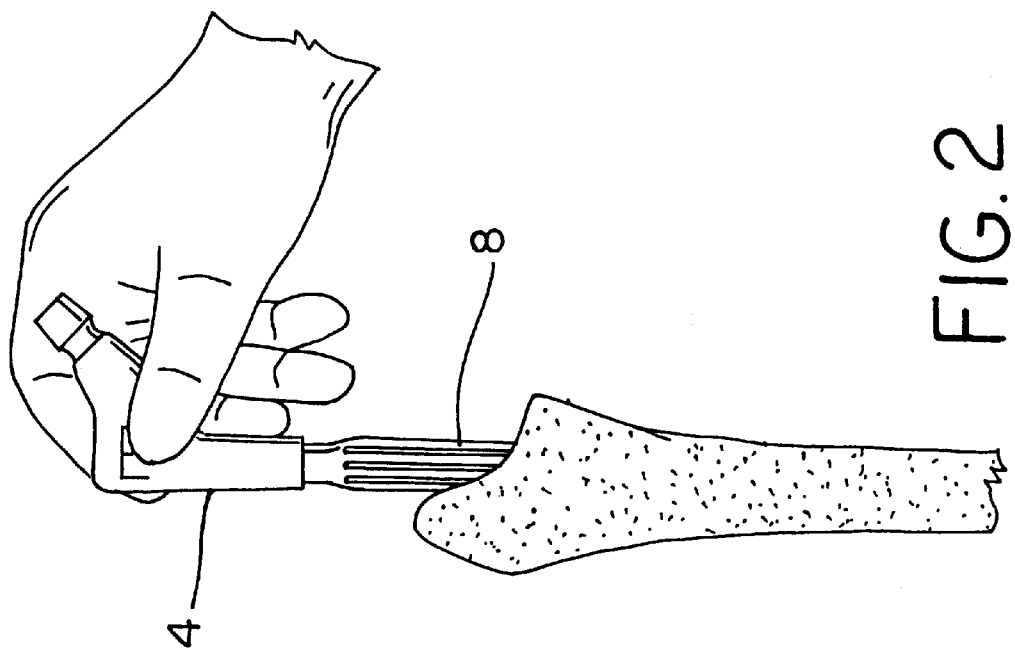
FIG. 2 is a front plan view of the implant of FIG. 1 being inserted into a bone.
Figure 1:
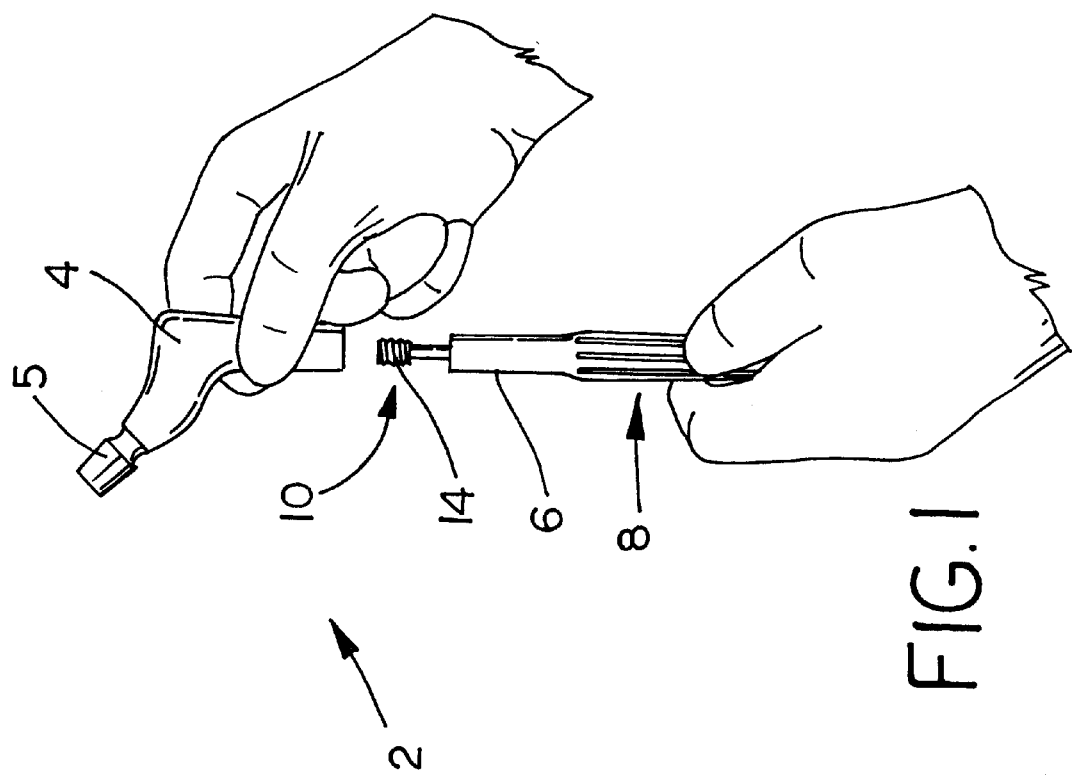
FIG. 1 is a front plan view of a modular implant being assembled.
Figure 4:
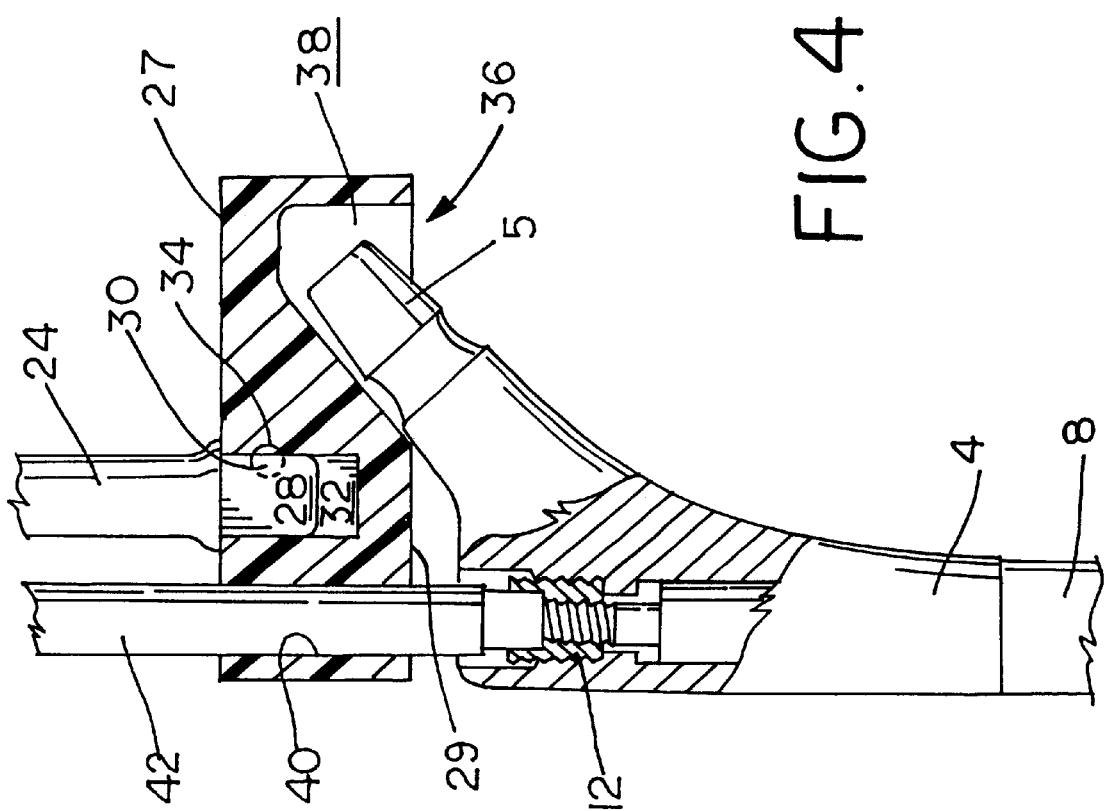
FIG. 4 is a partially sectioned front plan view of the wrench assembly of FIG. 3 engaging the implant of FIG. 1.

FIGS. 1 and 2 depict a modular implant 2 having a proximal body component 4 and a distal stem component 6. The body and stem components engage along a locking taper 8. A threaded coupling 10 further secures the components. In the illustrative embodiment, a retaining nut 12 engages a threaded stud 14 to compress the body 4 and stem 6 into secure engagement. In the illustrative embodiment, a femoral hip implant is shown in which the proximal body 4 includes a neck taper 5 (FIG. 4) for receiving a ball head (not shown) to engage an acetabular socket. It should be understood that the wrench assembly of the present invention can also be advantageously used with many other kinds of implants where it is desirable to retain the implant while applying a torque to the implant.

Figure 5:
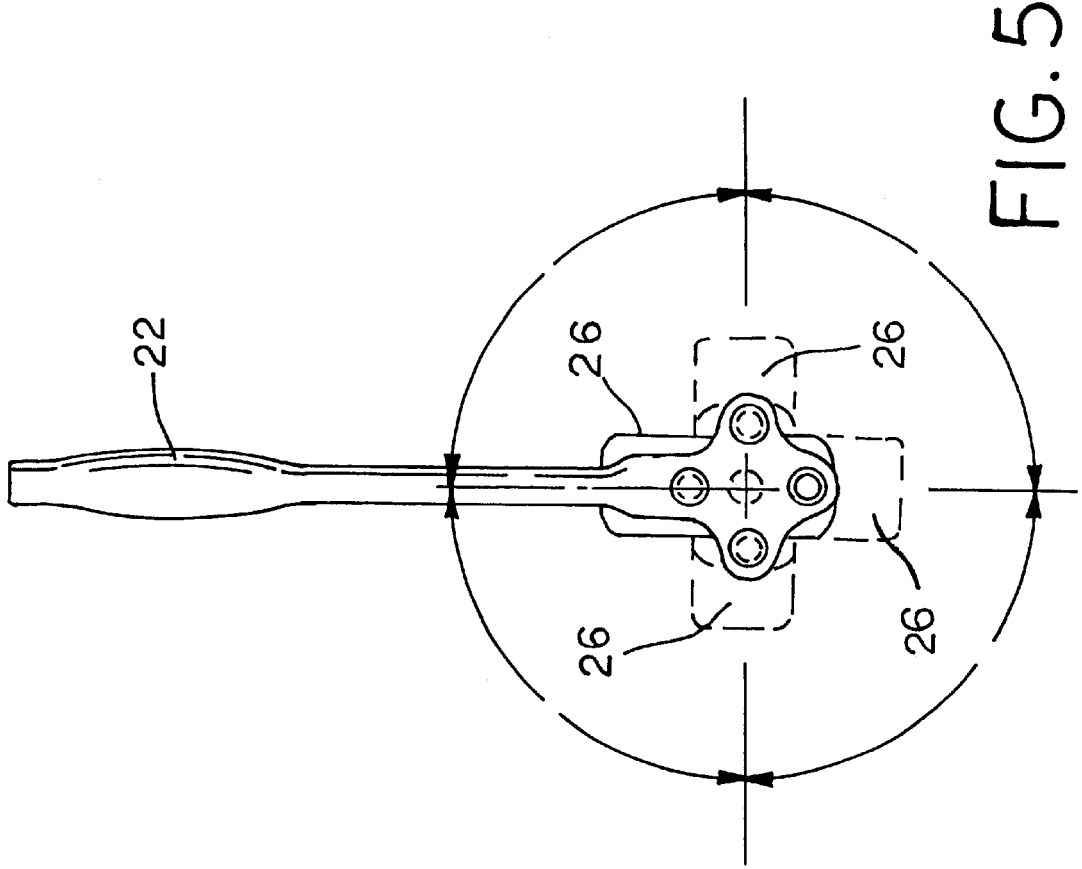
FIG. 5 is a top plan view of a portion of the wrench assembly of FIG. 3 showing alternate assembled positions.

FIGS. 3–9 depict a wrench assembly 20 for retaining the implant 2 while applying a torque to the retaining nut 12. The wrench assembly 20 includes a handle 22 having a socket shaft 24 depending from it. The handle 22 and socket shaft 24 are joined together in torque transmitting relation. Preferably the handle 22 and shaft 24 are welded together. However, they can advantageously be joined in a detachable manner such as with a snap-fit arrangement. Preferably handle 22 is perpendicular to shaft 24. A socket 26 is coupled to the socket shaft 24 in a torque transmitting relation. Preferably the socket shaft has a polygonal end section 28 with a ball detent 30 receivable in a corresponding polygonal recess 32 formed in the socket 26. A ball detent receiving recess 34 formed in the side of the polygonal recess 32 cooperates with the ball detent 30 to permit the end section 28 to snap into the recess 32. In this way the socket 26 is removably retained on the socket shaft 24. The socket 26 can advantageously be snapped onto the socket shaft 24 in a plurality of distinct positions corresponding to the number of sides of the polygonal end section 28 and polygonal recess 32 as will be described in more detail below. In the illustrative embodiment, the end section 28 and recess 32 have four sides permitting four orientations of the socket 26 relative to the shaft 24 as shown in FIG. 5.

The socket has an implant engaging portion 36 for engaging the implant in torque transmitting relation. In the embodiment shown, the implant engaging portion comprises a slot 38 shaped to receive the neck taper 5 of the illustrative hip implant proximal body 4. In this embodiment, the slot is formed opposite the socket shaft 24 so that the handle 22 and socket shaft 25 engage the socket on a first side 27 and the implant 2 engages the socket on a second side 29 opposite the first side. Thus, the handle projects away from the implant and is positioned for easy reach. The socket has a through hole 40 extending from the first side 27 to the second side 29. The through hole 40 is aligned with the portion of the implant that is intended to be torqued. In the illustrative embodiment, the through hole 40 is aligned with the retaining nut 12. Preferably the socket 26 is made of a material that will not mar the implant 2. Polymers are particularly preferable and Delrin has been found to work well because of its being non-marring, strong and autoclavable.

A driving shaft 42 passes through the through hole 40 and engages the portion of the implant, in this example the retaining nut 12, in torque transmitting relation. An end of the driving shaft is knurled 43 to facilitate torquing the driving shaft by hand. A torque wrench 44 is engageable with the driving shaft 42 to facilitate applying a known torque to the implant. Preferably, the torque wrench 44 engages the driving shaft 42 with a square socket and ball detent. The torque wrench 44 has a handle 46 and a torque indicator 48 responsive to the flexing of the handle to indicate the amount of torque being generated at the engagement end 50 of the torque wrench 44.

In the illustrative embodiment, the wrench assembly 20 further includes a driving shaft 42 stabilizer 60. The stabilizer 60 forms an enlarged end of the handle 22 near the point where the socket shaft 24 is attached to the handle 22. A through hole 62 is formed in the stabilizer. The through hole 62 in the stabilizer aligns with the through hole 40 in the socket so that the driving shaft 42 can be inserted from the stabilizer through hole 62 to the socket through hole 40 and into engagement with retaining nut 12. The stabilizer 60 maintains the socket shaft 24 and driving shaft 42 in proper alignment with one another and with the implant. This is especially helpful where, as in the illustrative embodiment the driving shaft 42 and socket shaft 24 are relatively long to facilitate access to the surgical site. Preferably the stabilizer 60 includes a plurality of through holes 62, 62a, 62b, 62c in an angular array relative to the socket shaft. In cooperation with the hole array, the socket is selectively attachable to the socket shaft in alternate positions because of the polygonal engagement end 28 and recess 32. Each alternate position corresponds to each of the plurality of through holes in the stabilizer 60 such that in each alternate position the socket through hole 40 is aligned with a different one of the stabilizer through holes 62, 62a, 62b, 62c. The stabilizer 60 is shown as forming an enlarged end of the handle 22. However, it could also be located elsewhere within the wrench assembly 2, for example, on the socket shaft 24. The important aspects of the stabilizer's function is that it have a supporting portion such as through hole 62 aligned with the through hole 40 in the socket and that the through holes 40 and 62 be sufficiently spaced to stabilize the driving shaft 42 in use. For maximum stability, it is preferable that the socket shaft 24 and driving shaft 42 be parallel to one another, that driving shaft 42 fit closely within through holes 62 and 40, that handle 22 extend perpendicular to socket shaft 24, and that handle 46 extend perpendicular to driving shaft 42. With these preferred relationships, the wrench assembly 20 is easily maintained in secure engagement with the implant 2 to retain the implant 2 while applying an opposing torque to the retaining nut 12.

Figure 3:
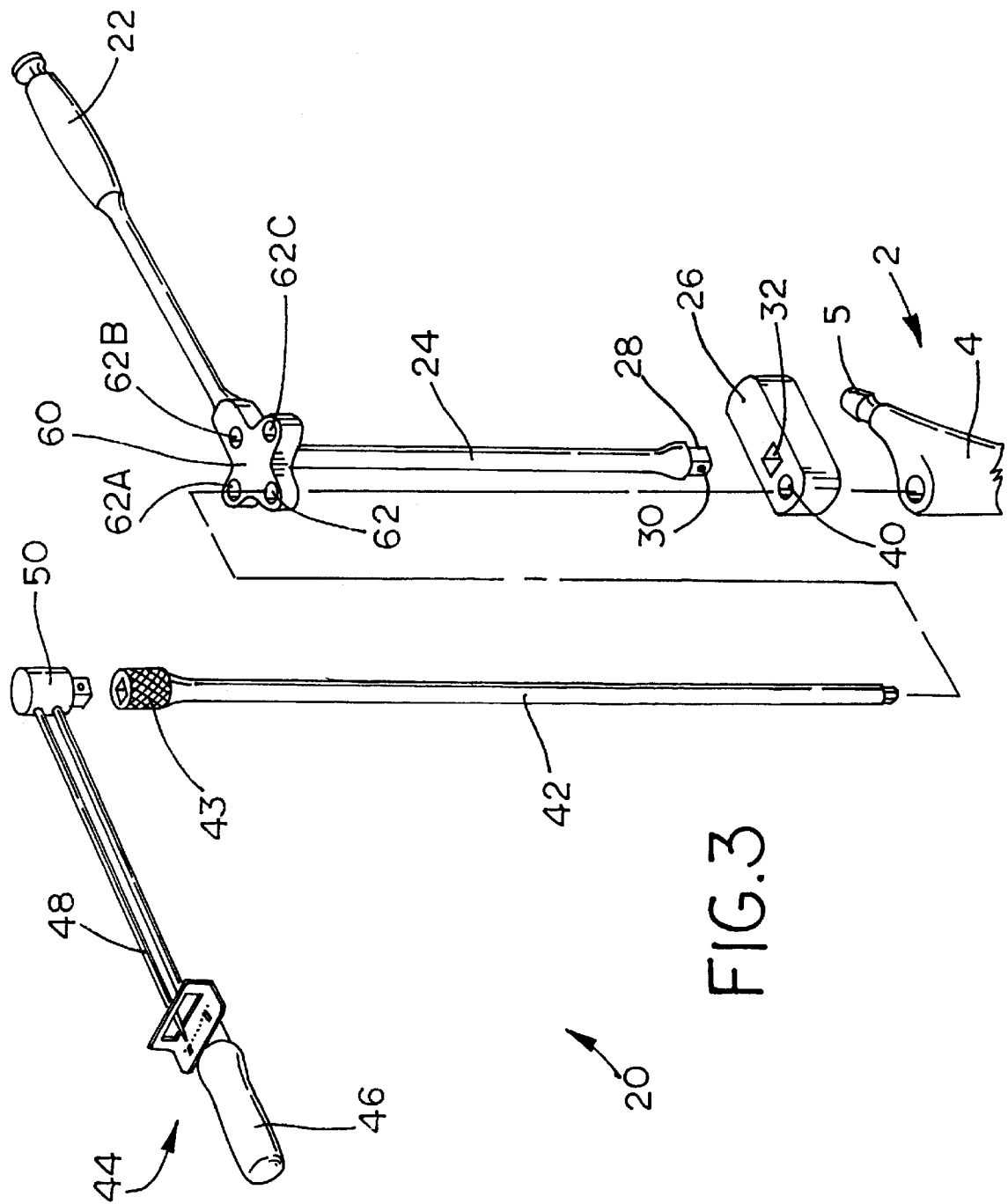
FIG. 3 is an exploded perspective view of an implant wrench assembly according to the present invention.
Figure 6:
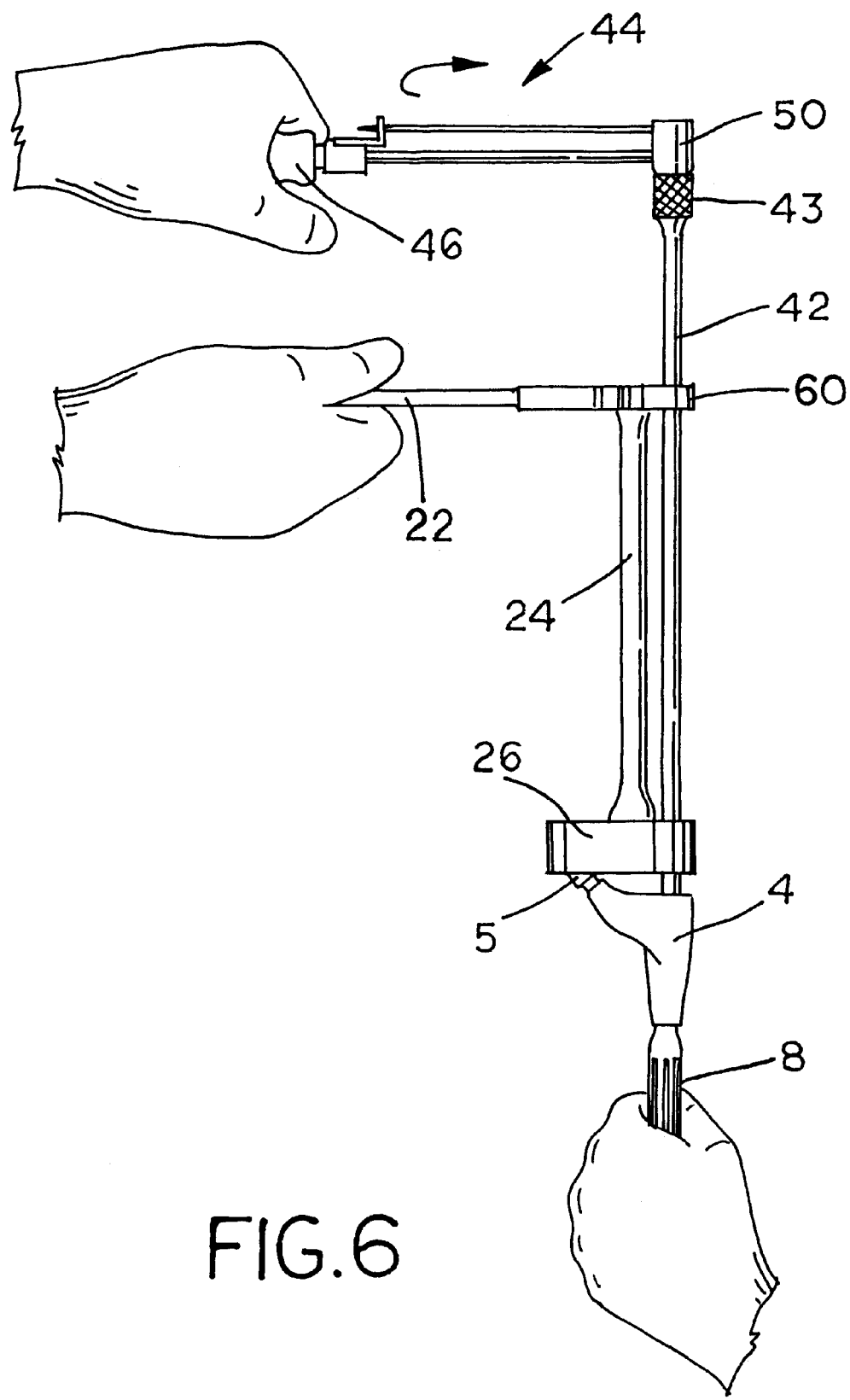
FIG. 6 is a front plan view of the wrench assembly of FIG. 3 being used to torque the implant of FIG. 1.
Figure 7:
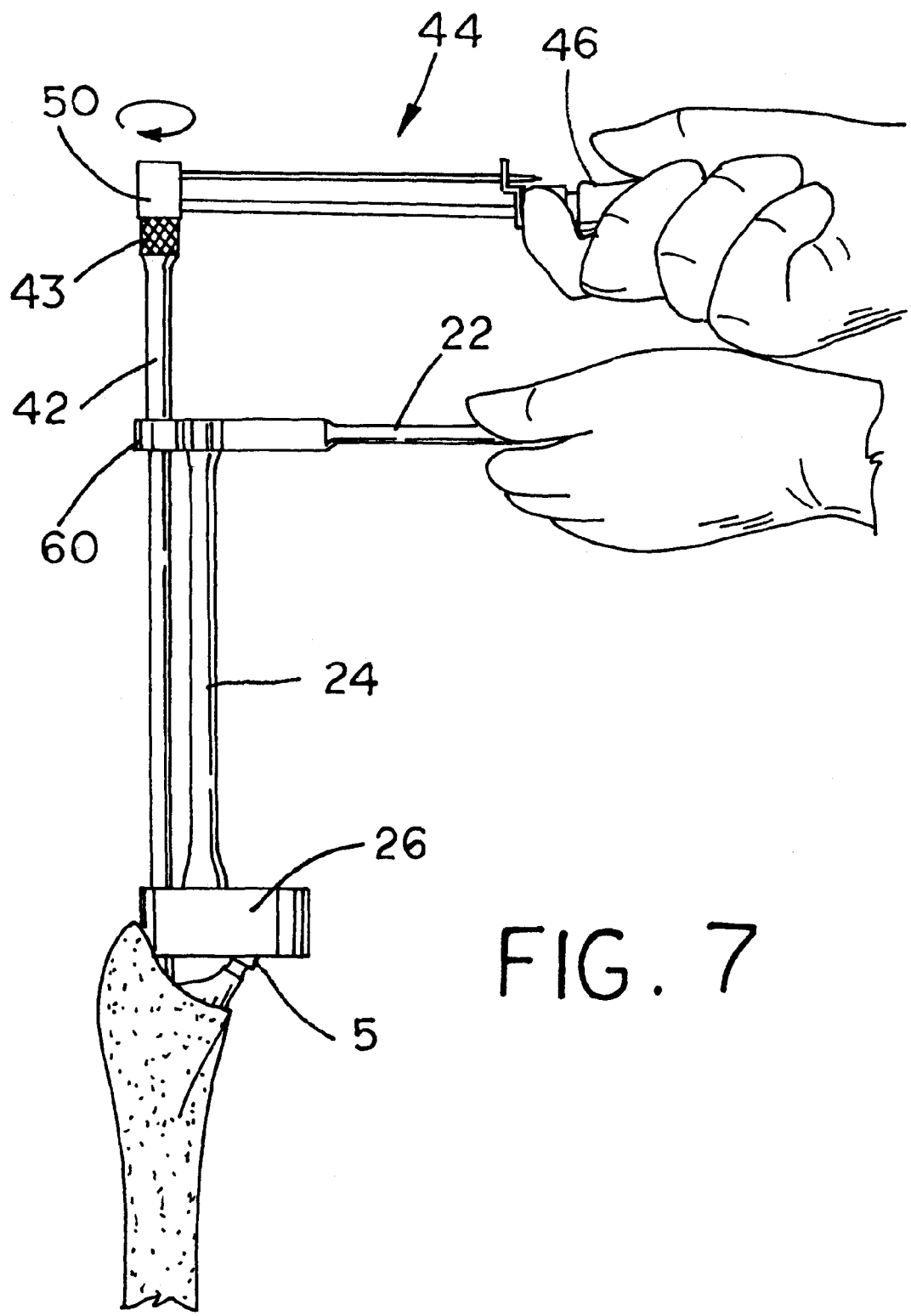
FIG. 7 is perspective view of the wrench assembly of FIG. 3 being used to torque the implant after being inserted into a bone as in FIG. 2.
Figure 8:
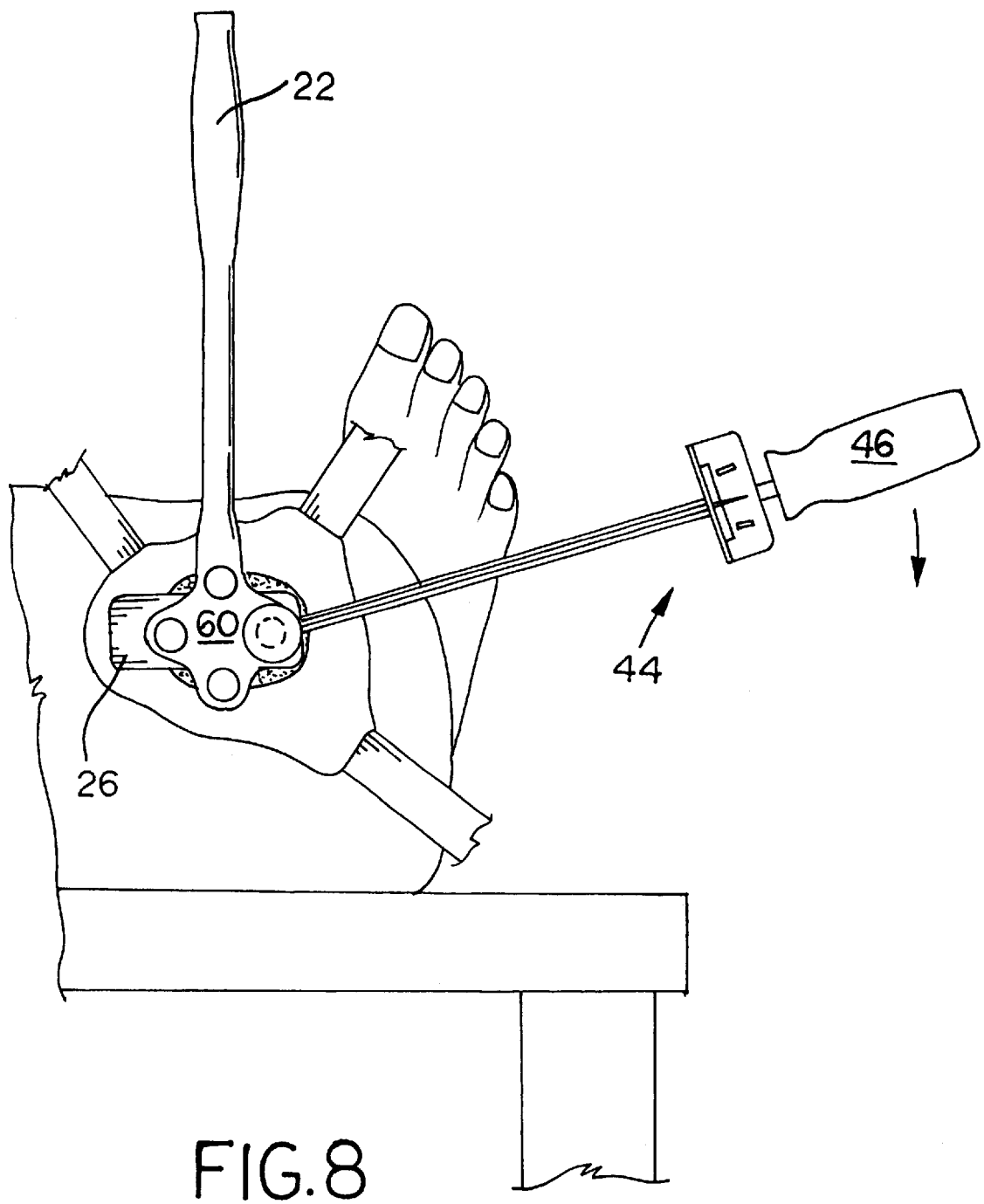
FIG. 8 is a top plan view of the wrench assembly of FIG. 3 being used interoperatively to torque an implant.
Figure 9:
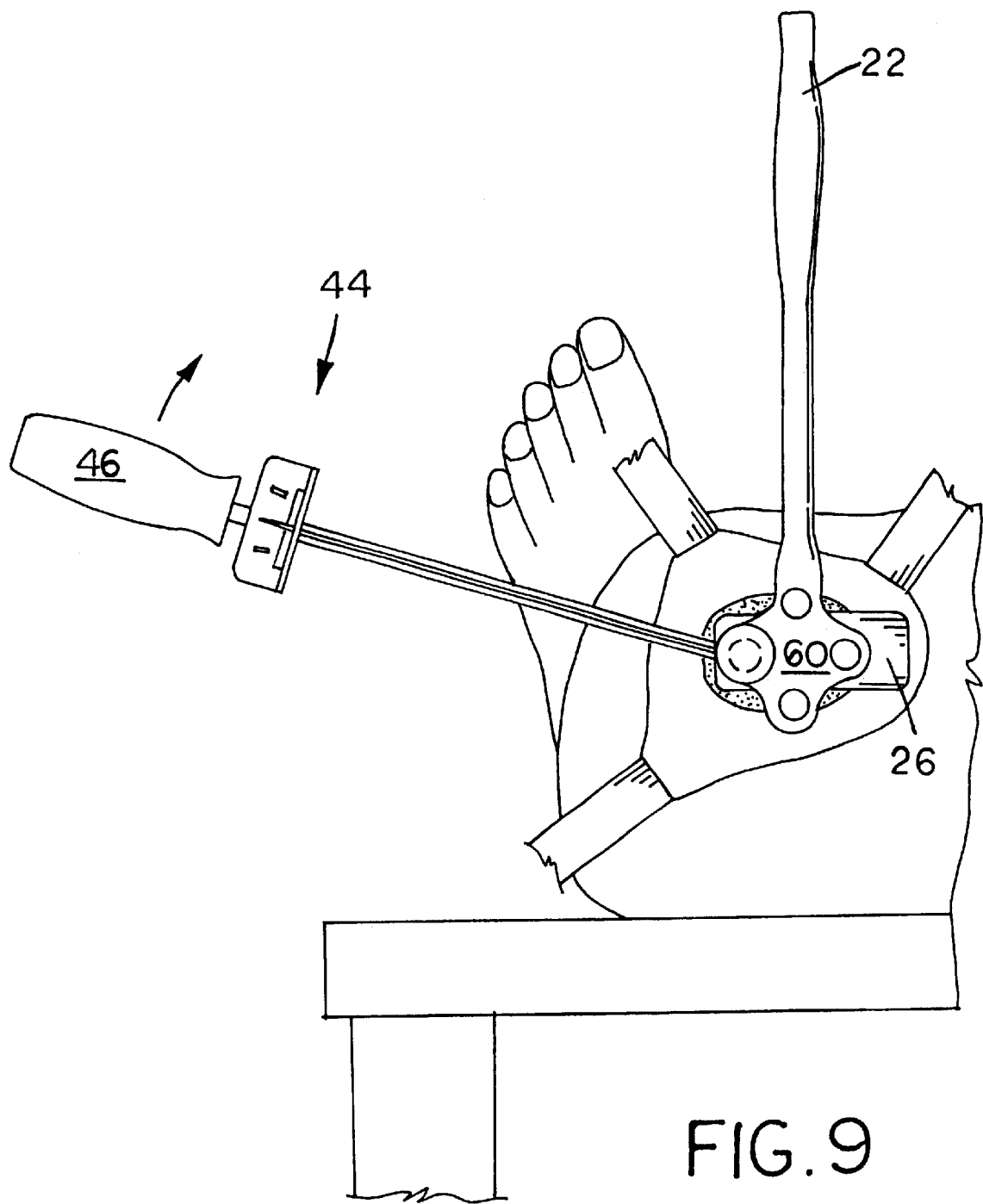
FIG. 9 is a top plan view of the wrench assembly of FIG. 3 being used interoperatively to torque an implant with the wrench assembled in an alternative position.

In use, the wrench is assembled as shown in FIG. 3. The implant 2 is engaged with the socket 26 and the driving shaft 42 is inserted through the socket through hole 40 to engage the retaining nut 12. As shown in FIGS. 6 and 7. With the handle 22 torsionaly fixed, the implant 2 is torsionaly fixed by way of the handle, socket shaft, socket and implant connections. A torque is then applied to the driving shaft 42 to tighten or loosen the retaining nut 12. The knurling 43 facilitates rapid threading of the retaining nut 12 on and off of the stud 14 by hand. A torque wrench 44 is engaged with the driving shaft to apply higher torque values for seating the retaining nut 12 or loosening it once it has been tightened. The implant is retained in its position by fixing the socket shaft handle 22, such as by holding it firmly in one hand. The retaining nut 12 can then be torqued without moving the implant out of position or stressing the bone.

Where a stabilizer 60 is provided, the driving shaft is inserted through both stabilizer through hole 62 and socket through hole 40. In the case of a stabilizer 60 with multiple through holes 62, 62a, 62b, 62c and a socket 26 attachable in corresponding alternate positions, the socket 26 is first attached to the socket shaft 24 so that the socket shaft handle 22 is aligned in a desirable direction. The direction may be selected, for example, so as to avoid soft tissue at the surgical site or to position the handle for easy reach. This may be different depending on whether the left or right side of the patient is being operated on as shown in FIGS. 8 and 9. The driving shaft 42 is then inserted through the appropriate stabilizer through hole 62, 62a, 62b, 62c to align with the socket through hole 40.

It will be understood by those skilled in the art that the foregoing has described a preferred embodiment of the present invention and that variations in design and construction may be made to the preferred embodiment without departing from the spirit and scope of the invention defined by the appended claims.

What is claimed is:

1. A wrench assembly for restraining an implant while applying a torque to the implant, the assembly comprising:
    a handle;
    a socket shaft depending from the handle in torque transmitting relation;
    a socket coupled to the socket shaft in torque transmitting relation, the socket having an implant engaging portion for engaging the implant in torque transmitting relation, the socket further having a through hole aligned with a portion of the implant; and
    a driving shaft passing through the through hole in the socket and engaging the portion of the implant such that with the handle torsionaly fixed, the implant is torsionaly fixed by way of the handle, socket shaft, socket and implant connections, and the driving shaft is movable relative to the socket to impart an opposing torque on the portion of the implant.

2. The wrench assembly of claim 1 further comprising a driving shaft stabilizer attached to one of the handle and the socket shaft, the driving shaft stabilizer being spaced from the socket and having a through hole aligned with the through hole in the socket, the driving shaft passing through both the hole in the stabilizer and the hole in the socket.

3. The wrench assembly of claim 2 wherein the driving shaft stabilizer includes a plurality of through holes in an angular array relative to the socket shaft, the socket being selectively attachable to the socket shaft in alternate positions, there being a distinct alternate position corresponding to each of the plurality of through holes in the driving shaft stabilizer in which each of the corresponding through holes in the driving shaft stabilizer is alternately aligned with the through hole in the socket.

4. The wrench assembly of claim 3 wherein the socket is coupled to the socket shaft with a square male/female coupling so that there are four distinct alternate positions of the socket relative to the shaft.

5. The wrench assembly of claim 4 wherein the male/female coupling includes a ball detent to positively retain the socket on the socket shaft.

6. The wrench assembly of claim 1 further comprising a torque wrench in driving connection with the driving shaft, the torque wrench having a handle and a torque indicator.

7. The wrench assembly of claim 1 wherein the socket is made of a material softer than the portion of the implant that the socket engages.

8. The wrench assembly of claim 1 wherein the socket is made of a polymer.

9. The wrench assembly of claim 1 wherein the driving shaft is in engagement with a threaded member coupled to the implant.

10. The wrench assembly of claim 9 wherein the driving shaft is in engagement with a retaining nut threadably engaged with the implant.

11. A wrench assembly for restraining a multicomponent hip implant while applying a torque to a fastener connecting the multiple components together, the hip implant including a distal stem component and a proximal body component, the proximal body component having a tapered neck portion, the assembly comprising:
   a handle;
   a socket shaft depending from the handle in torque transmitting relation, the socket shaft and handle being approximately perpendicular to one another;
   a socket coupled to the socket shaft in torque transmitting relation, the socket having a portion for engaging the neck taper portion of the implant in torque transmitting relation, the socket further having a through hole aligned with the fastener; and
   a driving shaft passing through the through hole in the socket and engaging the fastener such that with the handle torsionaly fixed, the implant is torsionaly fixed by way of the handle, socket shaft, socket and implant connections, and the driving shaft is movable relative to the socket to impart an opposing torque on the fastener.

12. The wrench assembly of claim 11 further comprising a driving shaft stabilizer attached to one of the handle and the socket shaft, the driving shaft stabilizer being spaced from the socket and having a plurality of through holes arranged in an angular array relative to the socket shaft, the socket being selectively attachable to the socket shaft in alternate positions, there being a distinct alternate position corresponding to each of the plurality of through holes in the driving shaft stabilizer in which each of the corresponding through holes in the driving shaft stabilizer is alternately aligned with the through hole in the socket, the driving shaft passing through the aligned holes.

13. The wrench assembly of claim 11 wherein the neck taper engaging portion of the socket includes a notch shaped to receive the neck taper.

14. The wrench assembly of claim 11 wherein the socket is made out of a polymer.

15. A method for restraining an implant while applying a torque to the implant, the method comprising the steps of:
   providing a wrench assembly comprising a handle, a socket shaft depending from the handle in torque transmitting relation, a socket coupled to the socket shaft in torque transmitting relation, the socket having an implant engaging portion for engaging the implant in torque transmitting relation, the socket further having a through hole;
   engaging the socket with the implant;
   inserting the driving shaft through the through hole;
   engaging the driving shaft with a portion of the implant; and
   applying opposing torque to the handle and driving shaft.

16. The method of claim 15 further comprising the steps of:
   providing the wrench assembly with a driving shaft stabilizer attached to one of the handle and the socket shaft, the driving shaft stabilizer being spaced from the socket and having a plurality of through holes arranged in an angular array relative to the socket shaft, the socket being attachable to the socket shaft in alternate positions, there being a distinct alternate position corresponding to each of the plurality of through holes in the driving shaft stabilizer in which each of the corresponding through holes in the driving shaft stabilizer is alternately aligned with the through hole in the socket;
   aligning the through hole in the socket with the portion of the implant;
   attaching the socket to the socket shaft so that the handle is pointing in a desirable direction;
   selecting the hole in the stabilizer that is aligned with the hole in the socket; and
   inserting the driving shaft through the aligned holes to engage the portion of the implant.

* * * * *